United States Patent [19]  [11] 4,046,575
Boie et al.  [45] Sept. 6, 1977

[54] COLOR PHOTOGRAPHIC MATERIAL CONTAINING 2-EQUIVALENT YELLOW COUPLERS

[75] Inventors: Immo Boie, Cologne; Dieter Lowski, Bergheim, Erft, both of Germany

[73] Assignee: AGFA-Gevaert, Aktiengesellschaft, Germany

[21] Appl. No.: 476,388

[22] Filed: June 5, 1974

[30] Foreign Application Priority Data

June 9, 1973 Germany ............................ 2329587

[51] Int. Cl.$^2$ .............................................. G03C 1/40
[52] U.S. Cl. .................. 96/100 N; 96/56.2; 96/56.3; 96/56.4; 96/56.5; 260/319.1; 260/326.16
[58] Field of Search ...................... 96/100, 56.2, 56.3, 96/56.4, 56.5

[56] References Cited

U.S. PATENT DOCUMENTS

| 3,617,291 | 11/1971 | Sawdey | 96/100 |
| 3,730,722 | 5/1973 | Inove et al. | 96/56.3 |
| 3,900,483 | 8/1975 | Fujimatsu et al. | 96/100 |

FOREIGN PATENT DOCUMENTS 2,213,461  11/1972  Germany ................. 96/100

Primary Examiner—J. Travis Brown
Attorney, Agent, or Firm—Connolly and Hutz

[57] ABSTRACT

A light-sensitive color photographic material containing at least one silver halide emulsion layer and a 2-equivalent yellow coupler which carries at the coupling position a 5-membered heterocyclic ring with at least one nitrogen atom which nitrogen atom is attached to the coupling position of the yellow coupler and which ring has in the position adjacent to the said nitrogen atom an ethylenic double bond which forms part of an olefinically unsaturated or of an aromatic 5-membered heterocyclic ring, which ring can be split off in the coupling reaction. The new 2-equivalent yellow couplers are easy to prepare, highly reactive and photographically substantially inert.

9 Claims, No Drawings

COLOR PHOTOGRAPHIC MATERIAL CONTAINING 2-EQUIVALENT YELLOW COUPLERS

This invention relates to new 2-equivalent yellow couplers, a process for their preparation and their use in color photographic materials.

It is known to produce colored photographic images by developing the exposed silver halide in a light-sensitive silver halide emulsion layer with an aromatic developer substance which contains primary amino groups in the presence of color couplers. The color couplers react wih the oxidized color developer to form an image dye which corresponds to the silver image.

In subtractive three-color photography a light-sensitive photographic multilayer material which contains a red, a green and a blue sensitized silver halide emulsion layer is generally used in which color development carried out using suitable color couplers results in a cyan, a magenta and a yellow dye image respectively.

The couplers used to form the cyan dyes are generally phenols or naphthols, the couplers used for the formation of magenta dyes are generally pyrazolones and the couplers used to form the yellow dyes are generally compounds which contain a methylene group with two carbonyl groups attached. The dyes formed by coupling are azomethines, indamines or indophenols, depending on the composition of the coupler and the developer. The conventional yellow couplers contain an active methylene group which reacts with the oxidized color developer during the process of color development. This reaction requires four equivalents of developable silver halide and these couplers are therefore known as 4-equivalent couplers. Other couplers are known which contain a methylene group in which one hydrogen is substituted by a group or substituent which can be split off in the coupling reaction. In this case, only two equivalents of developable silver halide are required to form the dye. These couplers are therefore known as 2-equivalent couplers. The following splittable groups or substituent have been proposed for yellow couplers:

1. Halogen, as described, for example, in French Pat. Specifications No. 991,453 and 869,169; U.S. Pat. Specifications No. 2,728,658 and 3,277,155 and British Pat. Specification No. 1,351,395.

2. The group OR in which R = alkyl, aryl or a heterocyclic group or an acyl group, e.g. as described in British Pat. Specification No. 1,092,506; French Pat. Specifications No. 1,411,385 and 1,385,696 and in U.S. Pat. Specifications No. 3,447,928 and 3,408,194.

3. A group SR as described, for example, in British Pat. Specification No. 953,454 and U.S. Pat. Specification No. 3,265,506.

4. A group

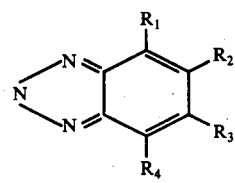

as described in U.S. Pat. Specification No. 3,617,291.

5. The groups SO₃H and SCN as described in British Pat. Specification No. 638,039 and in U.S. Pat. Specification No. 3,253,924.

6. A group

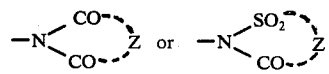

as described in German Offenlegungsschriften Nos. 2,163,812; 2,213,461 and 2,057,941.

The advantage of 2-equivalent couplers compared with 4-equivalent couplers is known in principle and may be described as follows: The quantity of silver halide required to form a given quantity of dye is about half the quantity required in the case of a 4-equivalent coupler so that a smaller quantity of silver halide may be used for preparing the light-sensitive recording material. A thinner emulsion layer may therefore be used, and this in turn has an advantageous effect on the power of resolution and sharpness of the photographic material.

Among the 2-equivalent yellow couplers known in the art which contain the above mentioned removable groups, those which contain halogen as splittable substituent have proved in practice to be particularly suitable because, when color development is carried out in a photographic material, the reactivity of the 2-equivalent yellow coupler must be sufficiently rapid to ensure satisfactory color densities even when very short processing methods are employed.

In practice, however, 2-equivalent yellow couplers which contain fluorine as splittable substituent have in practice not become established because of difficulty in preparation. 2-equivalent yellow couplers which contain chlorine as splittable substituent, on the other hand, frequently have a deleterious effect on the photographic properties of the silver halide emulsion. As described in British Pat. Specification No. 1,351,395, only certain yellow couplers based on benzoylacetanilide, which contain chlorine as removable substituent are photographically relatively inert and have only a slight influence on color fogging during development. However, the said couplers do not satisfy all the photographic requirements because, if the unprocessed photographic material is stored under moist, warm conditions, increased fogging on development cannot be completely excluded.

There have in practice been several attempts to find new 2-equivalent yellow couplers which would be available by preparation and the reactivity of which in color photographic development processes would be sufficiently high or at least comparable to that of 2-equivalent yellow couplers known in the art which contain fluorine or chlorine as splittable substituent. In this respect, however, the 2-equivalent yellow couplers known in the art whicn contain the splittable groups mentioned in paragraphs 2 to 5 above are distinctly inferior to the 2-equivalent couplers known in the art which contain fluorine or chlorine as splittable substituent.

It was therefore in practice necessary to find new, easily available 2-equivalent yellow couplers which would contain a new splittable group and the reactivity of which would be comparable to that of 2-equivalent couplers containing halogen as splittable substituent, and which would not deleteriously affect the photographic properties of the color photographic materials.

It has now been found that yellow couplers in which a hydrogen atom on the active methylene group is substituted by a nitrogen atom of a 5-membered, unsaturated heterocyclic ring can easily be prepared and constitute excellent 2-equivalent yellow couplers.

It is an important feature of the invention that the above mentioned 2-equivalent yellow couplers which contain a 5-membered nitrogen-containing unsaturated ring as splittable group are characterized in that the ring contains an ethylene double bond adjacent to the nitrogen atom through which the ring is linked to the yellow coupler group, which double bond forms part of an olefinically unsaturated or aromatic 5-membered heterocyclic ring.

Suitable 2-equivalent yellow couplers according to the invention are in particular those of the following general formula:

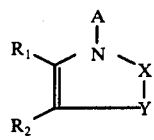

wherein
A represents a yellow coupler group substituted on the methylene group, e.g. an open chain ketomethylene coupler group such as an acylacetonitrile or acylacetyl coupler group;

X and Y represent the ring members required to complete a 5-membered unsaturated heterocyclic pyrrole, thiazolone-2- or oxazolone-2-ring, which ring members may themselves be substituted by any substituents alike or different, e.g. by alkyl or preferably by electro-negative substituents, such as halogen, nitro, cyan, sulfo, carbalkoxy, alkoxycarbonyl or trifluoroalkyl, or the ring members required to complete a condensed, preferably aromatic, 6-membered ring;

$R_1$ and $R_2$, which may be the same or different, represent the substituents commonly found in the chemistry of couplers, e.g. hydrogen, alkyl, alkoxy, alkylthio, aryl, acylamino, carbamyl, sulfamyl, sulfonamido, acyloxy, e.g. carbalkoxy, acyl, e.g. alkoxy-carbonyl, carboxy, nitro, halogen or cyano or $R_1$ and $R_2$ may together represent the ring members required to complete a 5- or 6-membered unsaturated carboxylic ring, e.g. a cyclopentene, cyclohexene, cyclopentadiene, cyclohexadiene or benzene ring, which rings may themselves be substituted with alkyl, alkoxy, alkylthio, aryl, acylamino, carbamyl, sulfamyl, sulfonamide, acyloxy, e.g. carbalkoxy, acyl, e.g. alkoxycarbonyl, carboxy, nitro, halogen, cyan or trifluoroalkyl groups.

If $R_1$ and $R_2$ together form the ring members required to complete a benzene ring, then the benzene ring is preferably substituted with at least one electro-negative substituent, in particular with halogen, nitro or cyano.

The equivalent coupler group A according to the invention which forms a yellow dye is derived from conventional 4-equivalent couplers which form a yellow dye. Preferred couplers according to the invention are those of the above general formula in which A represents an open chain ketomethylene yellow coupler group, e.g. acylacetonitrile- or acylacetyl coupler group in particular of the following formula I:

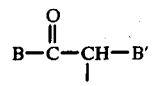

wherein
B represents an alkyl group preferably containing from 1 to 32 carbon atoms, more preferably 1 to 18 carbon atoms, which may be branched or straight chained, and, in the case of a secondary or tertiary alkyl group, the secondary or tertiary carbon atom is preferably directly attached to the carbonyl group; an alkoxyalkyl group, a dicycloalkyl group, a heterocyclic group or an aryl group which may be substituted by alkyl, preferably containing 1 to 18 carbon atoms, alkoxy containing preferably 1 to 18 carbon atoms, e.g. fluorine or bromine, acetamido, carbamyl, sulfamyl, sulfonamido or carboxy;

B' represents a cyano group or the group

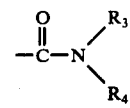

$R_3$ represents hydrogen or an alkyl group, preferably containing 1 to 5 carbon atoms, for example a methyl or ethyl group;

$R_4$ represents an alkyl group, preferably containing 1 to 18 carbon atoms, or preferably an aryl group, for example a phenyl group, which may be substituted with an alkyl group containing 1 to 18 carbon atoms, an alkoxy group containing 1 to 18 carbon atoms, halogen, e.g. fluorine or bromine, acylamino, carbamyl, sulfamyl, sulfoamido or carboxy.

The new yellow couplers according to the invention have a high coupling capacity, i.e. they produce dye images with a high color density and they are eminently suitable for use in light-sensitive silver halide emulsion layers of color photographic single or multi-layered materials.

The yellow couplers need not necessarily be incorporated in the light-sensitive layers but may be accommodated in a layer of binder adjacent to the light-sensitive silver halide emulsion layer.

Depending on the choice of substituents $R_1$, $R_2$, B or B' according to the definitions given above, the yellow couplers according to the invention may be used either as diffusionfast couplers or as non-diffusionfast couplers to form yellow color images in photographic materials. To obtain sufficiently high diffusionfastness, the substituents $R_1$, $R_2$, B or B', preferably B or B', are provided with groups which confer diffusionfastness, e.g. straight or branched chain alkyl groups containing 10 to 18 carbon atoms, or they may be substituted with alkyl substituted phenoxy groups which may be attached to the groups, B', $R_1$ or $R_2$ which may be aromatic either directly or indirectly, for example through —O—, —S—, —CONH—, —NHCO—, —SO$_2$NH—, —NHSO$_2$—, or other intermediate links.

If the couplers are required to be soluble in alkali, at least one of the groups B, B', $R_1$ or $R_2$ may carry groups which confer solubility in alkali, preferably sulfo groups.

Couplers according to the invention which are not diffusion-resistant are particularly suitable for use in developer solutions for developing the yellow dye image in exposed photographic color films which do not contain yellow coupler.

The 2-equivalent yellow couplers according to the invention which contain the heterocyclic splittable group of formula II

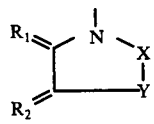
(II)

wherein $R_1$, $R_2$, X and Y have the meanings specified above, have, as already mentioned, an excellent coupling activity. Suitable 2-equivalent couplers according to the invention are, in particular, open chain ketomethylene yellow couplers which contain, as splittable group, an unsubstituted or substituted pyrrole, indole, indoxyl, pyrazole, imidazole, triazole, benzothiazolone-2 or benzoxazolone-2 ring, and which preferably contain at least one electro-negative substituent in the heterocyclic ring or in the condensed benzene ring. Particularly preferred 2-equivalent yellow couplers according to the invention contain, as their splittable group, an imidazole ring containing, in particular, short chain alkyl substituents with 1 to 4 carbon atoms, preferably methyl or electro-negative substituents such as nitro, chloro, carboxy, cyan or an alkoxycarbonyl group which contain 1 to 4 carbon atoms.

The following are examples of suitable yellow couplers according to the invention:

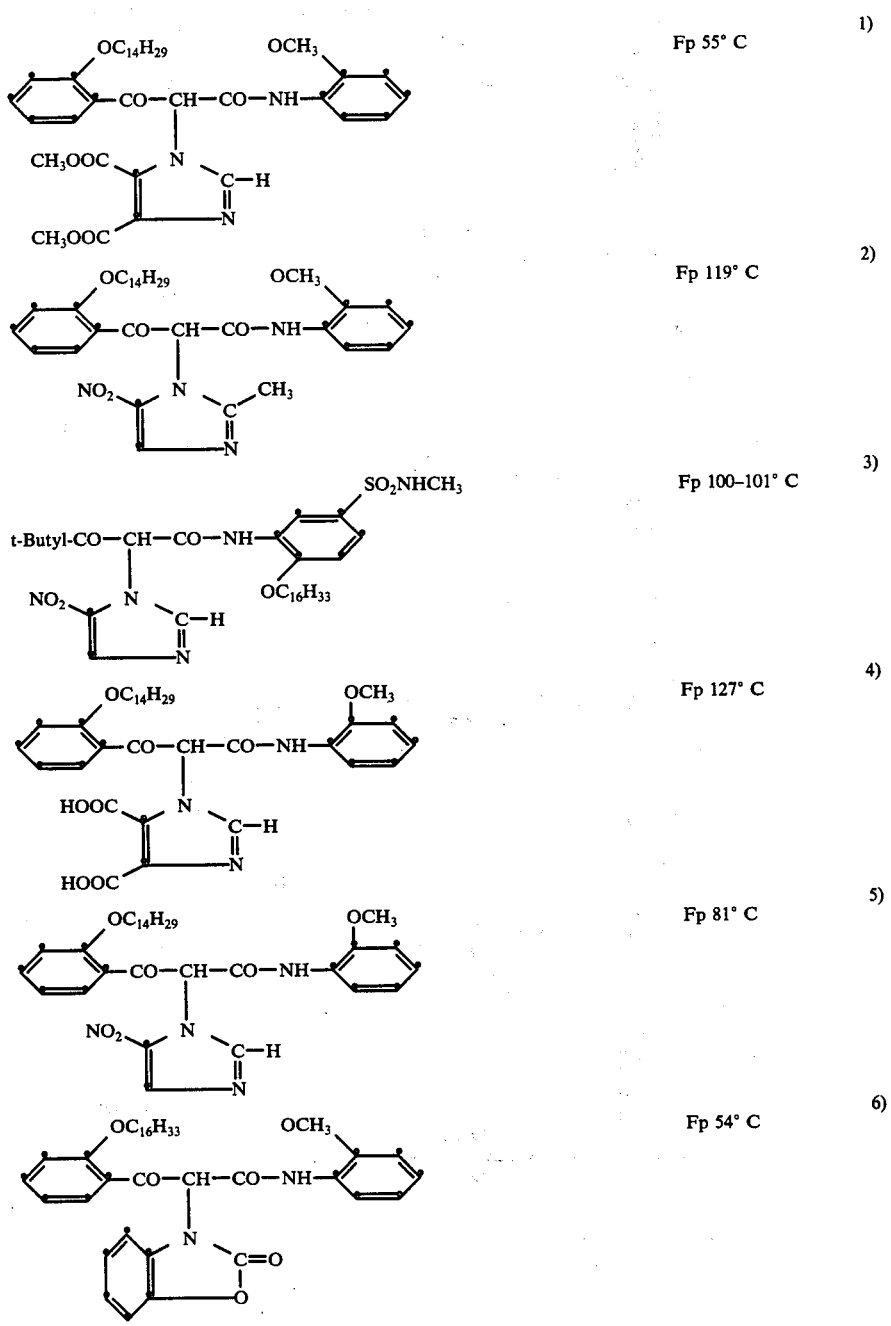

-continued
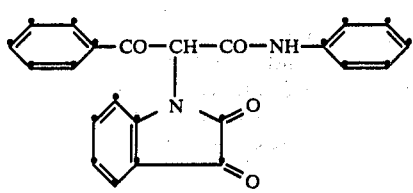 Fp 219° C 7)
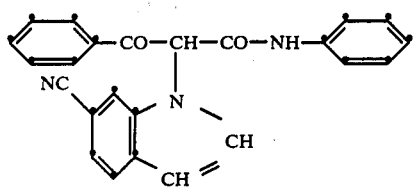 Fp 176° C 8)
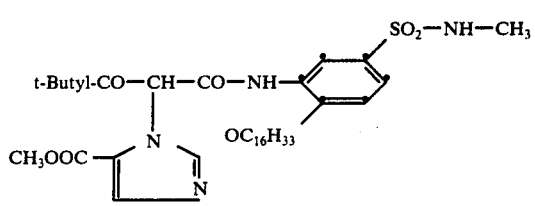 Fp 68° C 9)
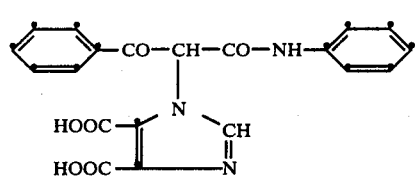 Fp 182° C 10)
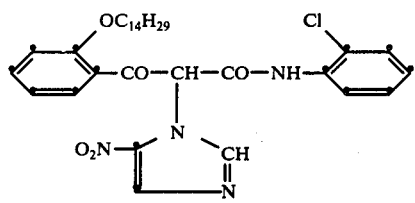 Fp 88–90° C 11)
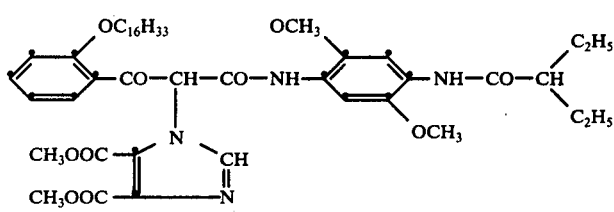 Fp 91° C 12)
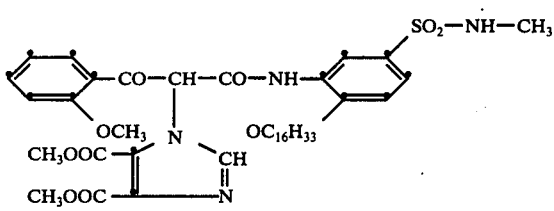 Fp 107° C 13)
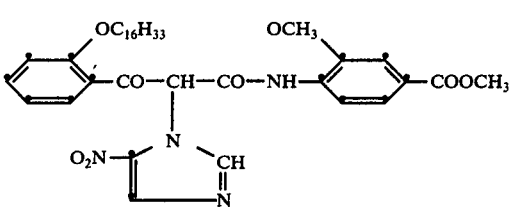 Fp 103° C 14)
15)

-continued

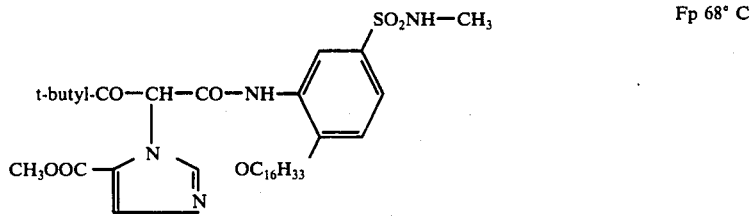

Fp 68° C

Those yellow couplers according to the invention which are diffusion resistant are highly emulsifiable, have excellent resistance to crystallization in the casting solution and in the photographic material and do not impair the photographic properties of the emulsions even under extreme conditions of storage.

The yellow couplers according to the invention can easily be prepared by reacting the corresponding 2-equivalent couplers which contain chlorine as removable substituent as represented by the formula A-Cl wherein A has the meaning indicated above, with a compound of formula III

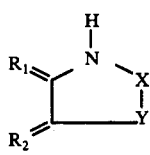

(III)

wherein X, Y, $R_1$ and $R_2$ have the meaning specified above, in the presence of a base in the usual manner, e.g. as described in German Offenlegungsschrift No, 2,213,461.

The reaction may be carried out in an aprotic solvent, e.g. acetonitrile or dimethylformamide, using as base either an aliphatic amine, e.g. triethylamine, or a basic heterocyclic compound such as pyridine or an alkali metal salt of an alcoholate such as sodium alcoholate.

It is unexpectedly found that the yellow couplers according to the invention can, in many cases, be obtained more easily and in higher yields by the above mentioned process than the couplers described in German Offenlegungsschrift No. 2,213,461, for example the o-alkoxy substituted benzoyl acetanilide couplers of German Offenlegungsschrift No. 2,213,461 can only be obtained by boiling them for days in acetonitrile and, even then in only moderate yields.

Furthermore, it has been found that when 2-equivalent couplers of the formula A-Cl are reacted with the compound of formula III wherein A, X, Y, $R_1$ and $R_2$ have the meanings specified above and with a base at temperatures of 20° to 100° C, preferably 40° to 80° C, in the presence of hexamethylphosphoric acid triamide as solvent, 2-equivalent couplers according to the invention are obtained in excellent yields and with a high degree of purity.

In the reaction according to the invention, the 2-equivalent coupler which contains chlorine as splittable group and the heterocyclic compound of formula III may generally be used in equimolar quantities although it is preferred to use a 1 to 200% molar excess of compound of formula III, based on the quantity of 2-equivalent coupler used.

It is generally sufficient to add the base in equimolar quantities, based on the compound of formula III. If desired, however, the base may also be used in a 1 to 200% molar excess.

The base used in the reaction according to the invention may be any of the basic compounds commonly used in the art, e.g. those defined above, although sodium methylate is preferred. The reaction according to the invention is generally carried out at temperatures of 20° to 100° C, preferably 40° to 80° C.

If desired, however, part of the hexamethylphosphoric acid triamide used as solvent, preferably not more than 50%, may be replaced by conventional polar solvents such as dioxane, ethers, alcohols, acetonitrile or dimethylformamide.

The quantity of hexamethyl phosphoric acid triamide used as solvent is not critical. It depends on the solubility of the reactants in the solution and can be determined by a few laboratory tests. Quantities of 5 to 100 ml of hexamethylphosphoric acid triamide per 1 g of coupler compound have generally been found to be sufficient.

The yellow couplers according to the invention can be precipitated from the reaction mixture in the usual manner by mixing them with a mixture of ice, water and hydrogen chloride, separated, washed and purified by dissolving the washed and dried reaction product in a solvent which is immiscible with water, e.g. chloroform or, preferably, in hot ether, and colorless crystals of the yellow couplers according to the invention can be obtained with an excellent degree of purity by adding petroleum ether and cooling the solvent mixture, so that no further purification processes such as recrystallization are generally required.

The reductive ring closure with zinc required for preparing the yellow couplers according to U.S. Pat. Specification No. 3,617,291 is generally difficult and results in only moderate yields and is extremely critical, particularly in some cases such as when the original coupler molecule or the removable group contains reducible groups such as nitro groups, and this method of preparation is therefore clearly inferior to the method of preparation of the yellow couplers according to the invention.

The preparation of coupler No. 5 according to the invention is described in detail below:

15 g of α-chloro-α-(2-tetradecyloxy)-benzoyl-2-methoxyacetanilide are dissolved in 100 ml of hexamethylphosphoric acid triamide, and 7 g of 4-nitroimidazole and 12 ml of 4 molar sodium methylate solution are added. After 3 hours' stirring at 40° C, the reaction mixture is poured on a mixture of ice and hydrogen chloride.

The reaction mixture is then filtered off, washed with water, dried on clay and dissolved in hot ether. After the removal of minor impurities by filtration, about 10 ml of petroleum ether are added to the hot filtrate which is then cooled. After suction filtration and washing with petroleum ether, 9.5 g of colorless crystals of coupler 5 are obtained. M.p. 81° C.

The preparation of the other couplers according to the invention may be prepared in a similar manner.

When preparing the light-sensitive color material according to the invention, the diffusion resistant yellow couplers according to the above general formula may be incorporated by any known technique in the casting composition of the silver halide emulsion layers or of other colloid layers which are in water-permeable relation thereto. For example, the water-soluble color couplers, i.e. those which contain one or more water-solubilizing groups such as a sulfo or carboxyl group (in acid or salt form) may be incorporated in the casting composition of the layer in question by applying them from an aqueous solution while those color couplers which are insoluble or insufficiently soluble in water may be applied from a solution in suitable water-miscible or immiscible high boiling or low boiling organic solvents or mixtures thereof. The resulting solution is then dispersed in a hydrophilic colloid composition, optionally in the presence of a wetting or dispersing agent this colloid composition constituting either all or only part of the binder of the colloid layer. The hydrophilic colloid composition may, of course, contain any other ingredients in addition to the colloid. The water-insoluble color couplers which contain fluorosulfonyl groups or carboxylic acid ester groups such as ethoxycarbonyl groups may also be converted by alkaline hydrolysis into the corresponding sulfonic acids or carboxylic acids which can be incorporated successfully in hydrophilic colloid compositions by applying them in the form of aqueous solutions of their alkali metal salts.

The solution of color coupler need not be directly dispersed or dissolved in the casting composition of the silver halide emulsion or some other water permeable layer. The solution may advantageously first be dispersed or dissolved in an aqueous light-insensitive solution of a hydrophilic colloid, where upon the resulting mixture, optionally after removal of the organic solvent used, is intimately mixed with the casting composition of the light-sensitive silver halide emulsion layer or other water permeable layer just before casting. Further details about particularly suitable techniques for incorporating color couplers in hydrophilic colloid layers of a photographic material may be found in published Dutch Pat. Applications No. 6,516,423; 6,516,424; 6,600,098; 6,600,099 and 6,600,628; Belgian Pat. Specification No. 750,889; U.S. Pat. Specification No. 2,304,940 and British Pat. Specification No. 791,219.

To prepare photographic color images according to the invention, an exposed silver halide emulsion layer is developed with an aromatic primary amino developer substance in the presence of a color coupler according to the invention. The developer substances used may be any color developer substances which are capable of yielding azomethine dyes. Suitable developer substances include aromatic compounds such as p-phenylenediamine and its derivatives, for example, N,N-dialkyl-p-phenylenediamine such as N,N-diethyl-p-phenylenediamine, N,N-dialkyl-N'-sulfomethylp-phenylenediamine and N,N-dialkyl-N'-carboxymethyl-p-phenylenediamine.

Suitable light-sensitive emulsions are emulsions of silver halides such as silver chloride, silver bromide or mixtures thereof, which may have a small silver iodide content of up to 10 mols-%, used in one of the conventional hydrophilic binders. The binder used for the photographic layers is preferably gelatin, although this may be partly or completely replaced by other natural or synthetic binders. Suitable natural binders are e.g. alginic acid and its derivatives such as its salts, esters or amides, cellulose derivatives such as carboxymethylcellulose, alkylcelluloses such as hydroxyethylcellulose, starch or its derivatives such as ethers or esters or carrageenates. The synthetic binders include polyvinyl alcohol; partly saponified polyvinyl acetate and polyvinylpyrrolidone.

The emulsions may also be chemically sensitized, e.g. by adding sulfur compounds such as allylisothiocyanate, allylthiourea and sodium thiosulfate at the stage of chemical ripening. Reducing agents may also be used as chemical sensitizers, e.g. the tin compound described in Belgian Pat. Specifications No. 493,464 and 568,687, or polyamines such as diethylene triamine or aminoethane sulfinic acid derivatives, e.g. according to Belgian Pat. Specification No. 547,323.

Noble metals such as gold, platinum, palladium, iridium, ruthenium or rhodium and compounds of these metals are also suitable chemical sensitizers. This method of chemcial sensitization has been described in the article by R. KOSLOWSKY, Z. Wiss. Phot. 46 (1951) 65 – 72.

The emulsions may also be sensitized with polyalkylene oxide derivatives, e.g. with a polyethylene oxide which has a molecular weight of between 1000 and 20,000 or with condensation products of alkylene oxide and aliphatic alcohols, glycols, cyclic dehydration products of hexitols, with alkyl-substituted phenols, aliphatic carboxylic acids, aliphatic amines, aliphatic diamines and amides. The condensation products have a molecular weight of at least 700, preferably more than 1000. These sensitizers may, of course, be combined in order to achieve special effects, as described in Belgian Pat. Specification No. 537,278 and British Pat. Specification No. 727,982.

The emulsions must have sufficient sensitivity in the blue spectral region. Non-sensitized emulsions whose sensitivity is due to the intrinsic sensitivity of the silver halides are generally used for this purpose although the silver halide emulsions may be spectrally sensitized in the blue region, e.g. by means of sensitizers of the kind described in British Pat. Specification No. 1,285,078.

The emulsions may contain the usual stabilizers, e.g. homopolar or salt-type compounds of mercury which contain aromatic or heterocyclic rings such as mercaptotriazoles, simple mercury salts, sulfonium mercury double salts and other mercury compounds. Azaindenes are also suitable stabilizers, particularly tetra- or penta-azaindenes and especially those which are substituted with hydroxyl or amino groups. Compounds of this kind have been described in the article by BIRR, Z. Wiss. Phot. 47 (1952) 2 – 58. Other suitable stabilizers include heterocyclic mercapto compounds, e.g. phenylmercaptotetrazole, quaternary benzothiazole derivatives and benzotriazole.

The emulsions may be hardened in the usual manner, for example with formaldehyde or halogenated aldehyde which contain a carboxyl group, such as mucobromic acid, diketones, methanesulfonic acid esters and dialdehydes.

The advantageous properties of the couplers according to the invention will be described below with the aid of some examples.

EXAMPLE 1

1. 2 mmol of Coupler 1 were dissolved in 3 ml of ethyl acetate and then emulsified in 20 ml of a 5% gelatin solution at 60° C, in known manner after the addition of 1 g of dibutylphthalate. The emulsion contained 0.16 g of sodium dodecylbenzene sulfonate.

The emulsion was then mixed with 85 g of a 7.5% gelatin solution in which 1.93 g of silver bromide were dispersed and the mixture was diluted with water until the viscosity is sufficiently reduced for casting.

When the emulsion has been cast on a transparent support layer of cellulose triacetate, the material prepared in this way was cut into several samples and exposed behind a grey step wedge.

The samples were developed for one, three or five minutes in a conventional color developer with contains diethyl-p-phenylenediamine as developer substance and bleached and fixed in the usual manner.

Color wedges were prepared in a similar manner except that, instead of 2 mmol of Coupler 1, 2 mmol of a compound of the following formula

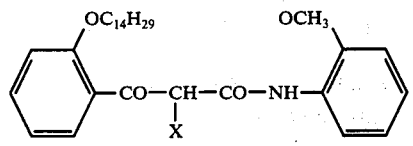

in which X has the meaning specified in Table 1 below were used.

The yellow densities of the individual samples were determined sensitometrically in the usual manner and the results obtained are shown in Table 1.

Table 1

| Coupler | X | 1 Min. | $D_{max}$ 3 Min. | 5 Min. |
|---|---|---|---|---|
| 1 | CH₃OOC—⟨N-CH=N⟩—CH₃OOC | 0.70 | 1.71 | 1.98 |
| 5 | O₂N—⟨N-CH=N⟩ | 0.532 | 1.4 | 2.02 |
| according to GB 1,351,395 | H | 0.126 | 0.308 | 0.574 |
| GB 1,351,395 | Cl | 0.516 | 1.72 | 1.96 |

As can be seen from Table 1, the reaction velocity of Couplers 1 and 5 according to the invention is comparable to that of comparison coupler 9 from British Pat. Specification No. 1,351,395 since the density values obtained with the various development times are approximately the same.

As can be seen from Table 1, the 4-equivalent coupler according to British Pat. Specification No. 1,351,395 is clearly inferior to the yellow couplers according to the invention.

EXAMPLE 2

Emulsions were prepared as described in Example 1 using, in each case, 2 mmol of the couplers shown in Table 2 below, and the emulsions were cast as described in Example 1.

The photographic materials obtained in this way were then divided into two protions, Sample A being developed for 5 minutes and processed as described in Example 1 and Sample B being stored in a heating cupboard for 7 days at 57° C and 34% relative humidity before being processed.

The Samples A and B are compared in Table 2 below, the criteria used for assessing them being the increase in basic fog values (ΔS) in relative values and the color density loss of Sample B compared with Sample A.

Table 2

| Coupler | X | ΔS | Color density loss |
|---|---|---|---|
| according to GB 1,351,395 | H | 0 | 0 |
| GB 1,351,395 | Cl | +0.33 | 0 |
| 1 | CH₃OOC—⟨N-CH=N⟩—CH₃OOC | +0.09 | 0 |
| 4 | HOOC—⟨N-CH=N⟩—HOOC | +0.01 | 0 |
| 5 | NO₂—⟨N-CH=N⟩ | +0.01 | 0 |

Table 2 shows that the heating cupboard stability of Couplers 1, 4, 5 and 8 according to the invention is clearly superior to that of the known couplers of the art described in U.S. Pat. Specification No. 3,617,291 and Coupler 9 disclosed in British Pat. Specification No. 1,351,395. The couplers according to the invention are distinguished by their excellent stability so that even when they are stored under moist warm conditions the photographic properties of the layer and in particular fogging are only immaterially affected.

We claim:

1. In a light-sensitive photographic material containing at least one silver halide emulsion layer and a 2-equivalent yellow coupler having an activated open-chain ketomethylene coupler structure in which one hydrogen of the methylene group is substituted by the nitrogen or a nitrogen-containing 5-membered heterocyclic ring that is photographically relatively inert except that it splits off from the coupler structure during chromogenic development, the improvement according to which the splittable nitrogen-containing five-membered heterocyclic ring is a C=C—N—C chain cyclized with C or O, and a benzene ring is fused to two carbons of the five-membered ring, adjacent the N.

2. In a light-sensitive photographic material containing at least one silver halide emulsion layer and a 2-equivalent yellow coupler having an activated open-chain ketomethylene coupler structure in which one hydrogen of the methylene group is substituted by a nitrogen of a heterocyclic group which group is photographically relatively inert except that it is split off during chromogenic development, the improvement according to which the splittable group is

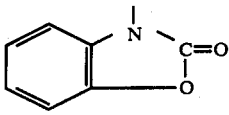

3. In a light-sensitive photographic material containing at least one silver halide emulsion layer and a 2-equivalent yellow coupler having an activated open-chain ketomethylene coupler structure in which one hydrogen of the methylene group is substituted by a nitrogen of a heterocylic group which group is photographically relatively inert except that it is split off during chromogenic development, the improvement according to which the splittable group is

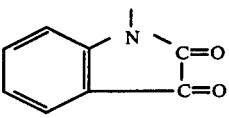

4. In a light-sensitive photographic material containing at least one silver halide emulsion layer and a 2-equivalent yellow coupler having an activated open-chain ketomethylene coupler structure in which one hydrogen of the methylene group is substituted by a nitrogen of a heterocyclic group which group is photographically relatively inert except that it is split off during chromogenic development, the improvement according to which the splittable group is an indole group bonded by its nitrogen to the methylene.

5. A silver halide emulsion containing a yellow coupler of the formula

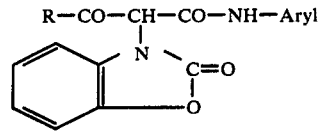

wherein R is aryl or t-butyl.

6. The combination of claim 1 in which the splittable group is substituted by at least one electronegative substituent of the class consisting of halogen, nitro, or cyano.

7. The combination of claim 2 in which the splittable group is substituted by at least one electronegative substituent of the class consisting of halogen, nitro, or cyano.

8. The combination of claim 3 in which the splittable group is substituted by a least one electronegative substituent of the class consisting of halogen, nitro, or cyano.

9. The combination of claim 4 in which the spittable group is substituted by at least one electronegative substitutent of the class consisting of halogen, nitro, or cyano.

* * * * *